United States Patent [19]
Bullimore

[11] Patent Number: 5,796,463
[45] Date of Patent: Aug. 18, 1998

[54] APPARATUS AND METHOD FOR IMPROVING THE OPERATION OF AN AUTOREFRACTOR

[75] Inventor: Mark A. Bullimore, Columbus, Ohio

[73] Assignee: The Regents of the University of California, Oakland, Calif.

[21] Appl. No.: 753,640

[22] Filed: Nov. 27, 1996

[51] Int. Cl.$^6$ ............................................... A61B 3/10

[52] U.S. Cl. ............................................ 351/205; 351/246

[58] Field of Search ........................... 351/200, 205, 351/246

[56] References Cited

U.S. PATENT DOCUMENTS 5,414,478  5/1995  Van Gelderen ............. 351/205 X
5,610,671  3/1997  Hosoi et al. ................. 351/200

OTHER PUBLICATIONS

Edlefsen et al., "Second Opinion: a computer expert system designed to aid in the determination of spectacle lens prescriptions", *J. of the Am. Optometric Assoc.* 66(10):620–630 (1995).

*Primary Examiner*—Huy Mai
*Attorney, Agent, or Firm*—Flehr Hohbach Test Albritton & Herbert LLP; William S. Galliani

[57] ABSTRACT

An apparatus to improve the operation of an autorefractor includes a first circuit to obtain objective refraction data and a second circuit to receive patient age data. An autorefractor output adjustment device is connected to the first circuit and the second circuit to combine the objective refraction data with a weight factor, which is assigned as a function of the patient age data and optometric clinical judgment, to obtain an eyeglass lens specification. The autorefractor output adjustment device may also rely upon eyeglass lens prescription data. The apparatus may be implemented in an autorefractor or it may be constructed as an external unit. The autorefractor output adjustment device may be implemented with a digital logic circuit executing a program or as a hardwired circuit.

26 Claims, 7 Drawing Sheets

APPARATUS AND METHOD FOR IMPROVING THE OPERATION OF AN AUTOREFRACTOR

BRIEF DESCRIPTION OF THE INVENTION

This invention relates generally to equipment that is used to derive spectacle prescriptions. More particularly, this invention relates to a technique of adjusting objective refraction data from an autorefractor to provide more accurate spectacle prescription specifications.

BACKGROUND OF THE INVENTION

Figure 1:
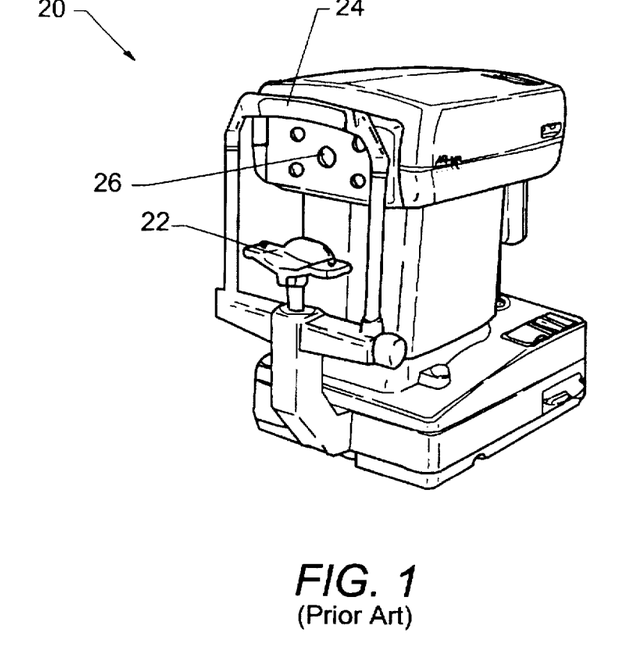
FIG. 1 is a front perspective view of an autorefractor in accordance with the prior art.

Autorefractors are used to estimate a patient's spectacle (eye glass) prescription. FIG. 1 illustrates an autorefractor 20 in accordance with the prior art. The autorefractor 20 includes a chin rest 22 and a forehead rest 24 which are used to position a patient's eyes in front of a measurement window 26.

Figure 2:
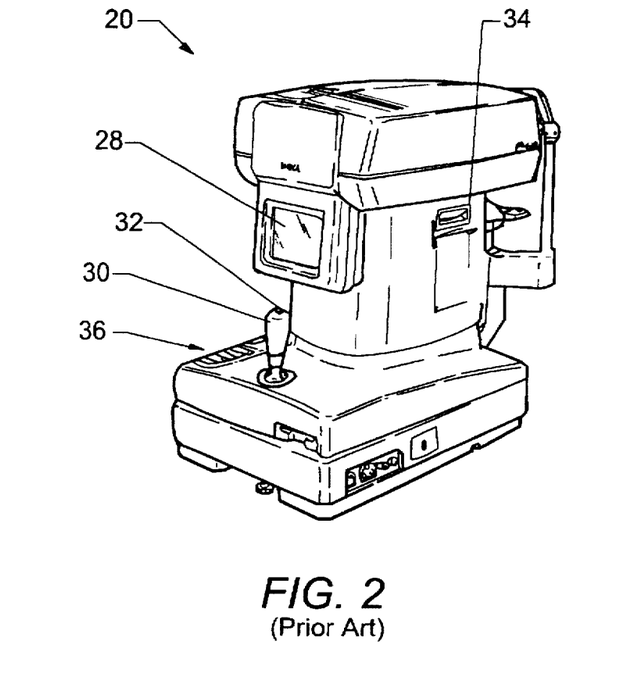
FIG. 2 is a rear perspective view of the autorefractor of FIG. 1.

FIG. 2 illustrates the opposite side of the autorefractor 20. A clinician uses a monitor to view the position of the patient's eyes in reference to an infrared measurement signal. The infrared measurement signal can be adjusted onto the patient's eye with a control stick 30. By pressing the measurement button 32, the autorefractor uses reflected data from the infrared measurement signal to produce objective refraction data including a sphere, cylinder, and axis values. The objective refraction data may be printed with printer 34. The objective refraction data is used to generate a spectacle prescription. Input specification devices 36 are used to set various parameters associated with the autorefractor 20.

Presently, the objective refraction data produced by an autorefractor is substantially refined by the clinician before the final prescription is issued. Most clinicians believe that prescribing spectacles directly from the autorefractor would lead to an unacceptably high number of dissatisfied patients. Consequently, clinicians frequently modify their refractive findings in order to maximize the likelihood of acceptance of the prescription by the patient. Such modifications include reducing the spherical or cylindrical components, shifting the cylinder axes towards 90 and 180 degrees, or reducing the difference in spherical equivalent between the two eyes. Factors which may also influence the clinician's prescription include the age of the patient and the previous prescription.

Currently, no "recommendations" are made to a clinician concerning modification of an autorefractor's output to generate a spectacle prescription. If the raw output could be modified based on the wisdom of experienced practitioners, then the instrument could be more successful in producing spectacle prescriptions which are acceptable to the patient. Furthermore, an instrument that provides a "smart" output would offer tremendous potential in countries where qualified and experienced clinicians are in limited supply. In short, improved autorefractor output could enable successful spectacle prescriptions without refinement from clinicians.

SUMMARY OF THE INVENTION

An apparatus to improve the operation of an autorefractor includes a first circuit to obtain objective refraction data and a second circuit to receive patient age data. An autorefractor output adjustment device is connected to the first circuit and the second circuit to combine the objective refraction data with a weight factor, which is assigned as a function of the patient age data and optometric clinical judgment, to obtain an eyeglass lens specification. The autorefractor output adjustment device may also rely upon eyeglass lens prescription data. The apparatus may be implemented in an autorefractor or it may be constructed as an external unit. The autorefractor output adjustment device may be implemented with a digital logic circuit executing a program or as a hardwired circuit.

The method and apparatus of the invention significantly improves the objective refraction data produced by an autorefractor. Consequently, the invention provides the capability of providing reliable spectacle prescriptions directly from an autorefractor without clinician refinement. Thus, the invention is particularly useful where qualified and experienced clinicians are in limited supply. The invention uses a computationally inexpensive technique to improve the autorefractor output data. Consequently, the invention can be conveniently incorporated into existing or new autorefractors without substantial additional cost.

BRIEF DESCRIPTION OF THE DRAWINGS

For a better understanding of the nature and objects of the invention, reference should be made to the following detailed description taken in conjunction with the accompanying drawings, in which.

Like reference numerals refer to corresponding parts throughout the several views of the drawings.

DETAILED DESCRIPTION OF THE INVENTION

Figure 3:
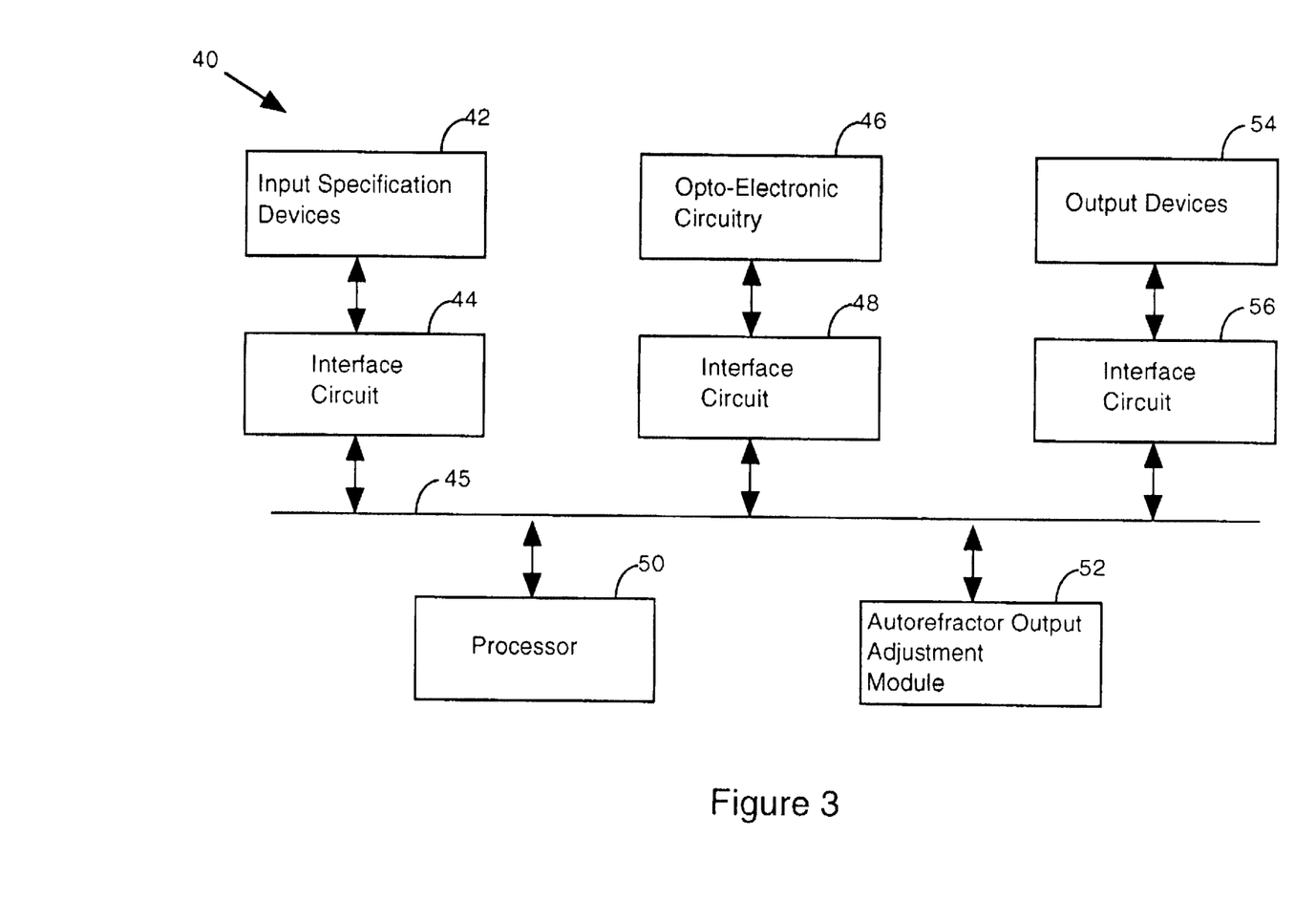
FIG. 3 is a schematic representation of an autorefractor in accordance with an embodiment of the invention.

FIG. 3 illustrates an autorefractor 20 constructed in accordance with an embodiment of the invention. The autorefractor 20 includes input specification devices 42 to set various parameters and provide input to the instrument. For example, the input specification devices 42 may include a button to specify a print operation and a keyboard to input patient age data. Buttons and keyboards of this type are known in the art. A standard interface circuit 44 is used to apply the information to a system bus 45.

A processor 50 is connected to the system bus 45. The processor 50 may be in the form of a central processing unit or other logic circuit. The processor 50 executes programs stored in memory. In particular, the processor 50 executes an autorefractor output adjustment module program 52 stored in memory.

Standard autorefractor opto-electronic circuitry 46 is used to collect objective refraction data in a known manner. The data is then passed through an interface circuit 48 to the processor 50. After the processor 50 and autorefractor output adjustment module 52 refine the objective refraction data, an eye glass lens specification is provided. That is, sphere, cylinder, and axis data describing an eye glass lens is generated by the autorefractor output adjustment module 52. This information is passed over the system bus 45 to an interface circuit 56, which passes the information to an output device 54. The output device 54 may be in the form of a printer, a monitor, a serial port, etc.

Figure 4:
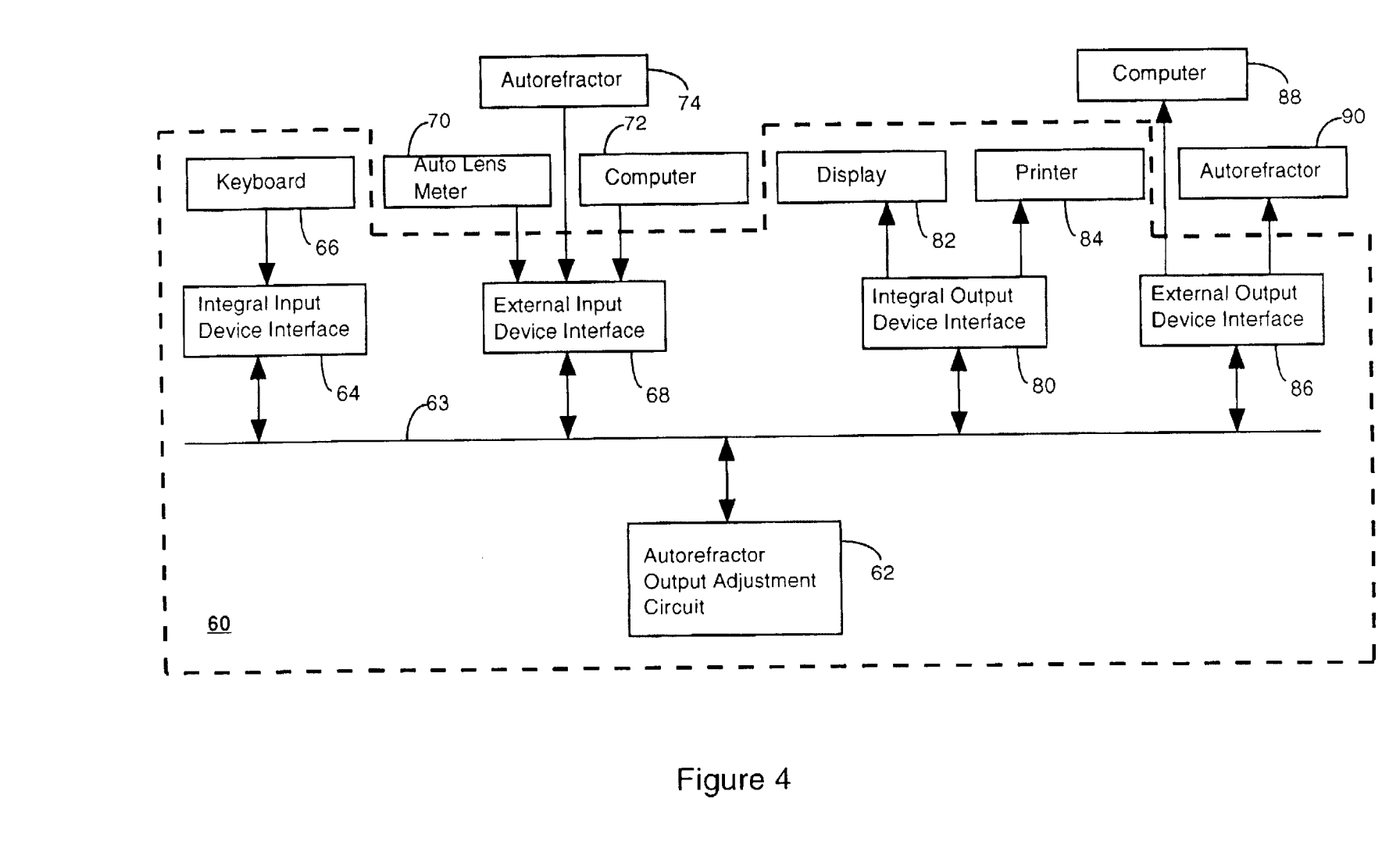
FIG. 4 is a schematic representation of an apparatus operated in connection with an autorefractor to improve the output of the autorefractor, in accordance with an embodiment of the invention.

FIG. 3 illustrates an embodiment of the invention incorporated into an autorefractor. FIG. 4 illustrates an embodiment of the invention which operates as an external unit. In particular, FIG. 4 illustrates an external autorefractor output processing apparatus 60 which includes an autorefractor output adjustment circuit 62. The autorefractor output adjustment circuit 62 may be implemented as a hardwired circuit. In the alternative, the apparatus 60 may be implemented with the processor 50 and autorefractor output adjustment module software 52 of FIG. 3.

In either embodiment, the apparatus 60 includes an integral input device interface 64 for connection to an input device such as a keyboard 66. The apparatus 60 also includes an external input device interface 68. The external input device interface 68 is used to interface with a variety of external devices. For example, the interface circuit 68 may be implemented as an RS-232C serial cable interface circuit for connection to an auto lens meter 70, which provides existing eyeglass lens prescription data to the apparatus 60. The interface circuit 68 may also be used for connection with an autorefractor 74, which provides objective refraction data. In addition, the eyeglass lens prescription data and objective refraction data may be provided by a computer 72.

The apparatus 60 also includes an integral output device interface 80, which is used to interface with output devices such as a display 82 and printer 84. The apparatus 60 is also preferably constructed to include an external output device interface 86, for connection with a computer 88 and autorefractor 90. The external input device interface 68 may be used to pass output to the autorefractor 74 and computer 72.

FIGS. 3 and 4 illustrate that the invention may be incorporated into an autorefractor or it may be used as an external unit with a variety of integral and external output devices. Thus, it should be appreciated that one skilled in the art can implement the autorefractor output adjustment device (52 or 62) of the invention into a variety of architectures. The operation of the invention merely requires a system architecture that allows input of patient age data and objective refraction data. As demonstrated in reference to FIGS. 3 and 4, this information may be obtained from input specification devices 42, opto-electronic circuitry 46, an autorefractor 74, a computer 72, or some other device. Preferably, the invention also relies upon eyeglass lens prescription data, which can be obtained from input specification devices 42, a keyboard 66, an auto lens meter 70, a computer 72 or by some other means. FIGS. 3 and 4 also demonstrate that the output of the apparatus of the invention may be applied to any number of devices, including output devices 54, display 82, printer 84, computer 88, autorefractor 90, or similar devices. In view of the foregoing, attention presently turns to a more detailed discussion of an autorefractor output adjustment device constructed in accordance with the invention.

Figure 5:
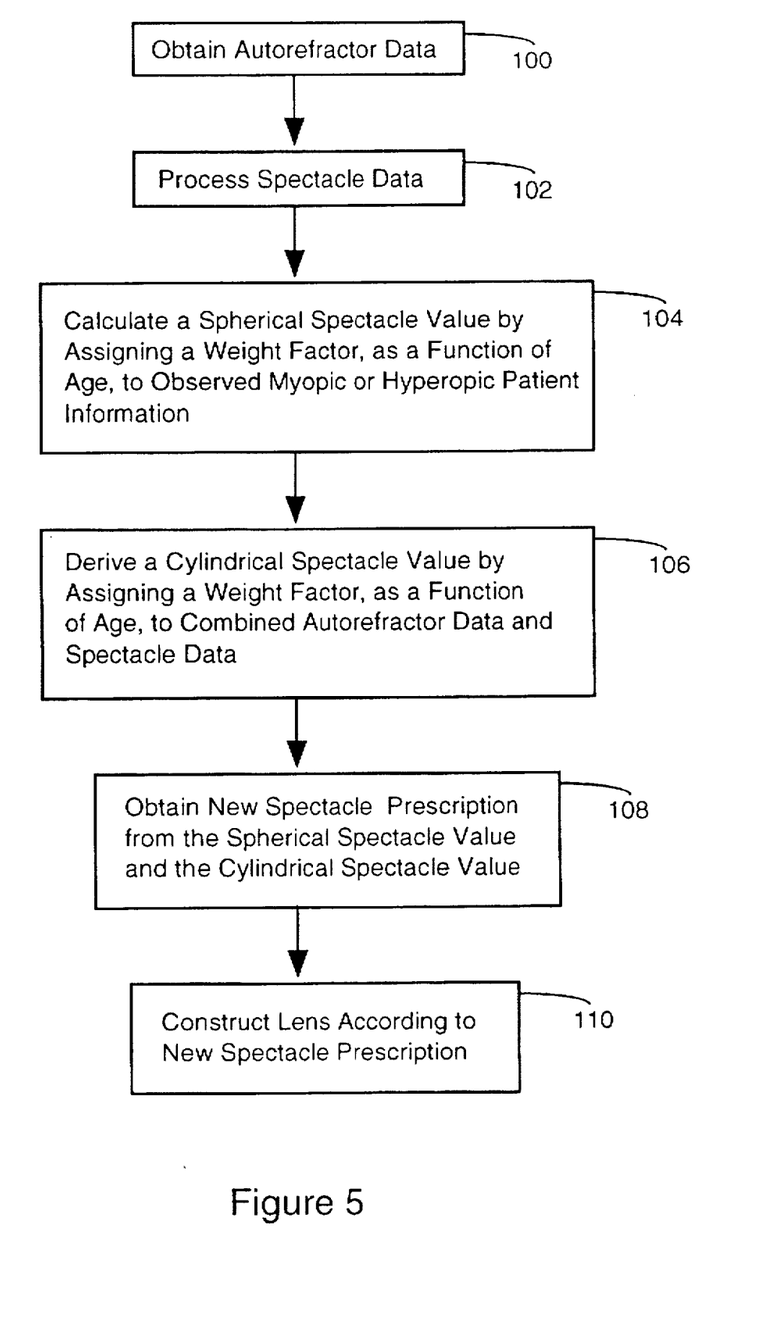
FIG. 5 is a set of processing steps performed in accordance with an embodiment of the invention.

FIG. 5 illustrates processing steps associated with an autorefractor output adjustment device in accordance with an embodiment of the invention. The first processing step illustrated in FIG. 5 is to obtain autorefractor data (step 100).

As indicated above, the objective refraction data from the autorefractor may be obtained from a variety of devices, including opto-electronic circuitry 46, keyboard 66, autorefractor 74, or computer 72.

The next processing step, which is optional, is to process spectacle data (step 102). As indicated above, the spectacle data may be secured from a variety of sources, including input specification devices 42, keyboard 66, auto lens meter 70, and computer 72.

The next processing step illustrated in FIG. 5 is to calculate a spherical spectacle value by assigning a weight factor, as a function of age, to observed myopic or hyperopic patient information (step 104). Subsequently, a cylindrical spectacle value is derived by assigning a weight factor, as a function of age, to combined autorefractor data and spectacle data.

Subsequently, a new spectacle prescription is obtained from the spherical spectacle value and the cylindrical spectacle value (step 108). Finally, a lens is constructed according to the new spectacle prescription (step 110).

The processing of FIG. 5 is more fully appreciated with a more detailed explanation of the individual processing steps. Those processing steps will now be more fully described in reference to a single lens prescription. The step of obtaining autorefractor data (step 100) results in a spherical value ($S_1$), a cylindrical value ($C_1$), and an axis value ($AX_1$). The step of processing spectacle data results in a spherical value ($S_2$), a cylindrical value ($C_2$), and an axis value ($AX_2$).

Figure 6:
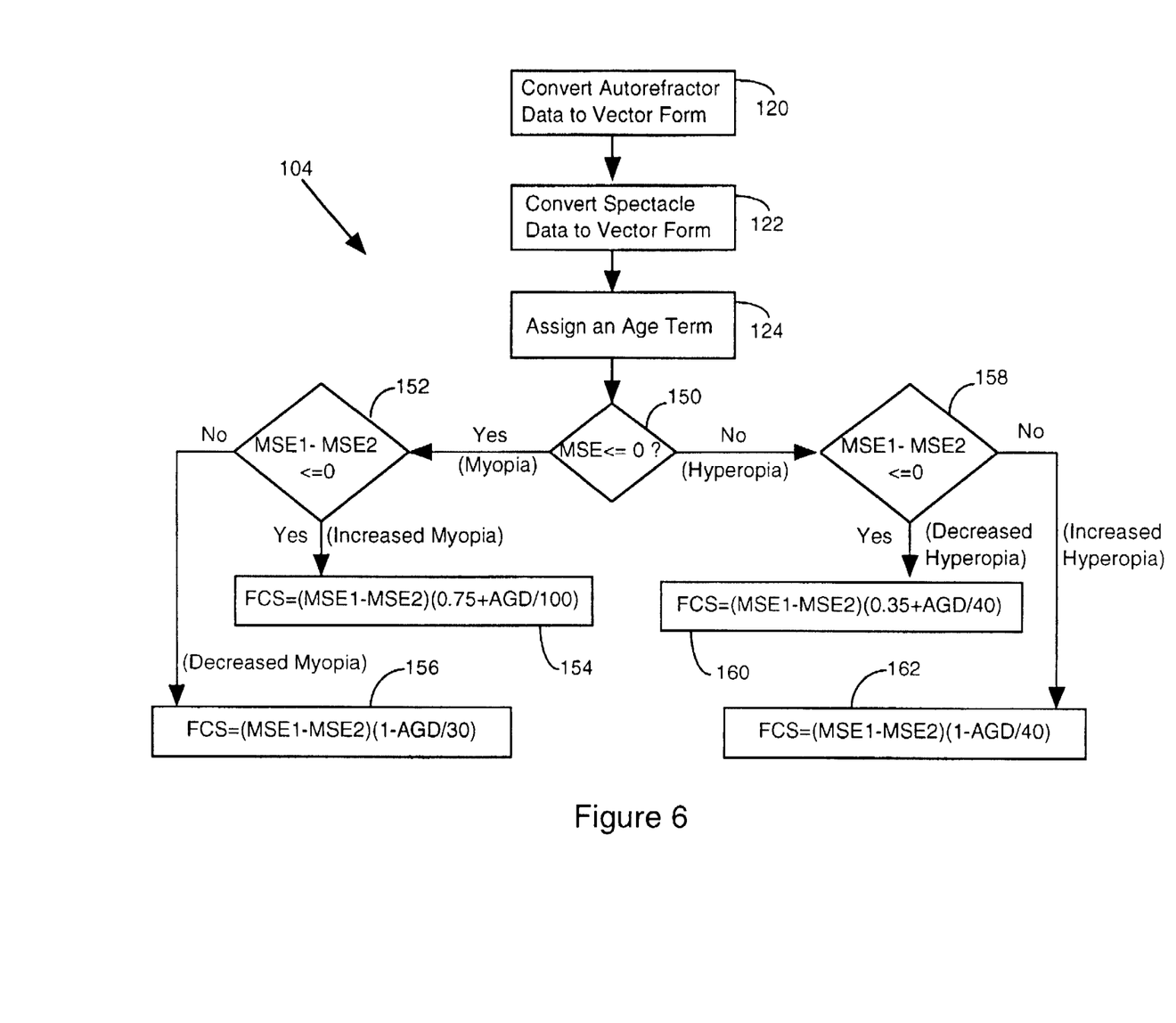
FIG. 6 illustrates a set of processing steps performed in accordance with one of the processing steps illustrated in FIG. 5.

The processing of step 104 is more particularly described in reference to FIG. 6. FIG. 6 illustrates that the first processing step is to convert the autorefractor data to vector form (step 120). This operation may be performed using the following equations.

| | |
|---|---|
| $MSE_1 = S_1 + (C_1/2)$ | (Equation 1) |
| $J0_1 = (C_1/2) \cos(AX_1 * \pi/90)$ | (Equation 2) |
| $J45_1 = (C_1/2) \sin(AX_1 * \pi/90)$ | (Equation 3) |

The $MSE_1$ term refers to the mean spherical equivalent, the $J0_1$ term refers to the cylinder power at 0°, and the $J45_1$ term refers to the cylinder power at axis 45°. Multiplication by $\pi/90$ provides a conversion to radians. The calculations may also be made using degrees.

The next processing step shown in FIG. 6 is to convert the spectacle data to vector form (step 122). This operation may be performed using the following equations.

| | |
|---|---|
| $MSE_2 = S_2 + (C_2/2)$ | (Equation 4) |
| $J0_2 = (C_2/2) \cos(AX_2 * \pi/90)$ | (Equation 5) |
| $J45_2 = (C_2/2) \sin(AX_2 * \pi/90)$ | (Equation 6) |

Figure 7:
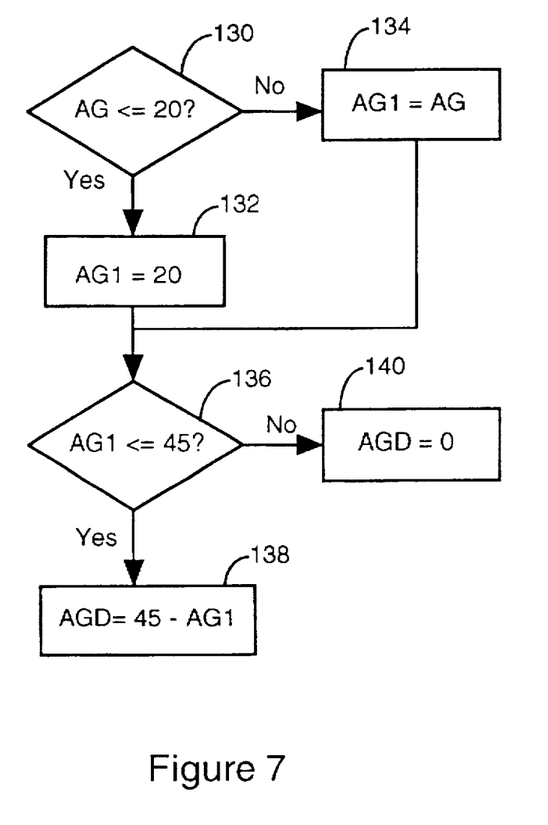
FIG. 7 illustrates a set of processing steps corresponding to one of the processing steps of FIG. 6.

The next processing step is to assign an age term to the age data (step 124). An implementation of this operation is shown in FIG. 7. Decision block 130 is used to determine whether the patient age data is less than or equal to 20. If so, a temporary age term of 20 is assigned to the variable $AG_1$ (step 132), otherwise the variable $AG_1$ is assigned the value of the age data (step (134). If the temporary age term $AG_1$ is less than or equal to 45, then the age term AGD is set to be the difference between 45 and the age data (step 138), otherwise the age term AGD is set to the value 0 (step 140).

In sum, the processing of FIG. 7 accomplishes the following. An individual that is older than 45 is assigned an age term AGD of zero. An individual that is 20 or younger is assigned an age term of twenty-five. For an individual between 20 and 45 years in age, the age term is set to difference between 45 and the individual's age. The assignment of an age term is part of the process of assigning a weight factor to the autorefractor output data, as will be more fully appreciated with the following discussion.

Returning to FIG. 6, the next processing step is to determine whether the mean spherical equivalent term $MSE_1$ derived from the autorefractor data is negative (step 150). If so, the patient has myopia and a decision is made to determine whether the myopia has increased or decreased (step 152). In particular, step 152 determines whether the difference between the mean spherical equivalent autorefractor data ($MSE_1$) and the mean spherical equivalent spectacle data ($MSE_2$) is less than or equal to zero. If less than or equal to zero, then an increased myopia term exists since the patient has experienced increased myopia. Therefore, the value indicating the increased myopia ($MSE_1-MSE_2$) is multiplied by a weight factor of (0.75+AGD/100), as shown at step 154.

For a young patient, the term AGD is equal to 25. Therefore, the weight factor is one (0.75+25/100). In other words, a full weight factor (1) is assigned to an increased myopia term in a young patient. For an old patient, the term AGD is equal to 0. Therefore the weight factor is 0.75 (i.e., 0.75+0/100). In other words, a substantial weight factor (0.75) is assigned to an increased myopia term in an old patient. The equation of step 154 demonstrates that between a young and old patient, the AGD term will vary, thus, the output will vary on a sliding scale between 1 and 0.75.

The general philosophy behind the weight factor assigned at step 154 is that a young patient has the ability to change eye focus, thus a full prescription change is justified. On the other hand, an older patient cannot tolerate an abrupt prescription change, thus the amount of change is softened with the weight factor. The actual values used in step 154 (and the remaining weight factors described herein) are derived from the clinical wisdom of the inventor and other clinical faculty at the University of California at Berkeley, School of Optometry. Thus, the weight factor embodies clinical judgment regarding a proper spectacle prescription given patient age data, objective refraction data, and eyeglass lens prescription data.

Returning to step 152, if the difference between the $MSE_1$ and $MSE_2$ terms is positive, then a decreased myopia term exists. Accordingly, a weight factor is assigned as shown at step 156. The calculated myopia difference term ($MSE_1-MSE_2$) is multiplied by a weight factor defined as (1-AGD/30). Thus, for a young patient the weight factor will be 0.17 (i.e., 1-25/30), whereas for an old patient the weight factor will be 1 (i.e., 1-0/30). In other words, the spherical spectacle value is calculated by assigning a full weight factor (1) to a decreased myopia term in an old patient, and a very small weight factor (0.17) to a decreased myopia term in a young patient. The weight factor slides for patients between 20 and 45 years in age.

The general philosophy embodied by the operation of step 152 is that if the autorefractor indicates that there is decreased myopia in a young patient, then the autorefractor has probably made an erroneous measurement, thus the changed myopia term should be largely ignored. In the case of an older person, myopia may decrease. Consequently, the weighting reflects that factor, thereby allowing a more aggressive change in prescription for older patients.

Returning now to step 150, if the objective refraction data ($MSE_1$) is greater than zero, then hyperopia exists. A decision is then made to determine whether the hyperopia has increased or decreased (step 158). If there is decreased hyperopia, the applied weight factor is (0.35+AGD/40), as shown at step 160. Thus, for a young patient, the weight factor is 0.975 (i.e., 0.35+25/40), and the weight factor for an old patient is 0.35 (i.e., 0.35+0/40). In other words, a spherical spectacle value is calculated by assigning a substantially full weight factor (0.975) to a decreased hyperopia term in a young patient, and a small weight factor (0.35) to a decreased hyperopia term in an old patient. A sliding scale weight factor is applied to patients with ages between 20 and 45.

The weight factors reflect the fact that hyperopic prescriptions generally do not change markedly. This is especially so for an older patient, thus the weight factor reduces the prescription change factor. For a young patient, the change can be more aggressive because the focusing ability of a young patient will compensate as required.

If the hyperopia has increased, then the weight factor of step 162 is used. In this case, a young patient is assigned a weight factor of 0.375 (i.e., 1-25/40), while an old patient is assigned a weight factor of 1 (i.e., 1-0/40). Thus, a spherical spectacle value is calculated by assigning a full weight factor (1) to an increased hyperopia term in an old patient, and a small weight factor (0.375) to an increased hyperopia term in a young patient. A sliding scale weight factor is used for patients therebetween.

The weight factors reflect that an older patient needs a full change in prescription, whereas a young patient can get by with a small change in prescription.

Figure 8:
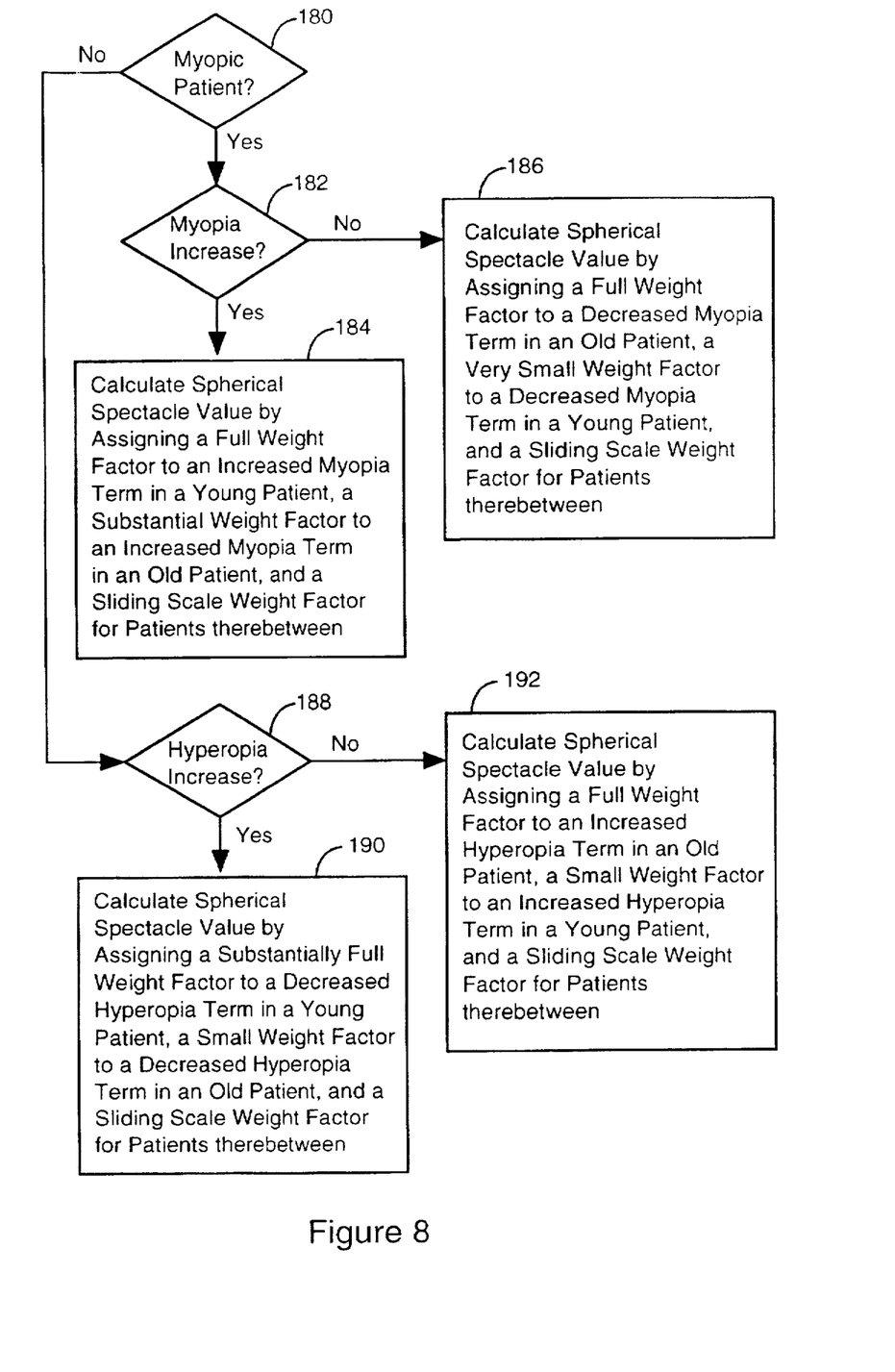
FIG. 8 illustrates a set of processing steps corresponding to processing steps illustrated in FIG. 6.

Steps 150-162 of FIG. 6 can also be characterized as shown in FIG. 8. In particular, in FIG. 8 step 180 corresponds to step 150 of FIG. 6, step 182 corresponds to step 152, step 184 corresponds to step 154, step 186 corresponds to step 156, etc.

The spherical spectacle calculation (step 104) has now been fully described. The next processing step shown in FIG. 5 is to derive a cylindrical spectacle value by assigning a weight factor, as a function of age, to combined autorefractor data and spectacle data. This operation may be performed using the following calculations.

$$FCJ_0=(J0_1-J0_2)(0.75+AGD/120)+J0_2 \qquad \text{(Equation 7)}$$

$$FCJ_{45}=(J45_1-J45_2)(0.5+AGD/60)+J45_2 \qquad \text{(Equation 8)}$$

The weight factor of Equation 7 (0.75+AGD/120) results in a weight factor of 0.96 for a young patient and a weight factor of 0.75 for an old patient. Similarly, in Equation 8, a weight factor of 0.9 is assigned for a young patient and a weight factor of 0.5 is assigned for an old patient. These weight factors result in relatively large prescription changes for young patients and relatively small prescription changes for old patients.

The next processing step shown in FIG. 5 is to obtain a new spectacle prescription from the calculated spherical spectacle value and cylindrical spectacle value. In other words, sphere, cylinder and axis terms are calculated from the vector quantities processed in steps 104 and 106. To express the new spectacle prescription in positive cylindrical power, the following equations are used.

$$MSE=FCS+MSE_2 \qquad \text{(Equation 9)}$$

Equation 9 indicates that the new mean spherical equivalent term (MSE) is a combination of the original mean spherical equivalent term of the existing prescription, plus a change factor (FCS) calculated in step 104. The MSE term is then used in a spherical calculation as follows.

$$SPH = MSE - SQRT((FCJ0)^2 + (FCJ45)^2)$$ (Equation 10)

The term SQRT indicates the square root of the quantity within the parentheses. A cylindrical calculation may then be made as follows.

$$CYL = 2*SQRT((FCJ0)^2 + (FCJ45)^2)$$ (Equation 11)

An axis value may be obtained with the following calculation:

$$\theta = 0.5*ATAN(|FCJ45/FCJ0|)*180/\pi$$ (Equation 12)

The following equations may be used to express the prescription in negative cylindrical terms.

$$MSE = FCS + MSE_2$$ (Equation 13)

$$SPH = MSE + SQRT((FCJ0)^2 + (FCJ45)^2)$$ (Equation 14)

$$CYL = -2*SQRT((FCJ0^2 + (FCJ45)^2)$$ (Equation 15)

$$\theta = 0.5*ATAN(|FCJ45/FCJ0|)*180/\pi + 90$$ (Equation 16)

The positive or negative cylinder prescription mode is preferably specified through the use of an input specification device 42 or keyboard 66.

If the patient is a first time spectacle wearer or existing prescription data is not otherwise available, then the spectacle data ($S_2$, $C_2$, $AX_2$) is set to zero. In this case, a positive cylinder prescription can be specified using the following equations.

$$SPH = MSE - 0.75SQRT((FCJ0)^2 + (FCJ45)^2)$$ (Equation 17)

$$CYL = *0.75SQRT((FCJ0)^2 + (FCJ45)^2)$$ (Equation 18)

Note that this operation includes a weight factor of 0.75. This weight factor softens or reduces the prescription.

To express the prescription of a first time spectacle wearer in negative cylinder mode, the following equations may be used.

$$SPH = MSE + 0.75SQRT((FCJ0)^2 + (FCJ45)^2)$$ (Equation 19)

$$CYL = -2*0.75SQRT((FCJ0)^2 + (FCJ45)^2)$$ (Equation 20)

Those skilled in the art will appreciate that the foregoing processing operations are relatively easy to implement in a computer program or hardwired circuit. Thus, the invention can be easily used with existing and new autorefractors to improve autorefractor output.

The foregoing description, for purposes of explanation, used specific nomenclature to provide a thorough understanding of the invention. However, it will be apparent to one skilled in the art that the specific details are not required in order to practice the invention. In other instances, well known circuits and devices are shown in block diagram form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following Claims and their equivalents.

I claim:

1. An apparatus to improve the operation of an autorefractor, comprising:
    a first circuit to obtain objective refraction data;
    a second circuit to receive patient age data; and
    an autorefractor output adjustment device connected to said first circuit and said second circuit to combine said objective refraction data with a weight factor, which is assigned as a function of said patient age data and optometric clinical judgment, to obtain an eyeglass lens specification.

2. The apparatus of claim 1 further comprising:
    an output device connected to said autorefractor output adjustment device to display said eyeglass lens specification.

3. The apparatus of claim 1 further comprising:
    a third circuit to receive eyeglass lens prescription data, said autorefractor output adjustment device processing said eyeglass lens prescription data to obtain said eyeglass lens specification.

4. The apparatus of claim 1 wherein said first circuit obtains said objective refraction data from opto-electronic circuitry of an autorefractor.

5. The apparatus of claim 1 wherein said first circuit obtains said objective refraction data from a computer.

6. The apparatus of claim 1 wherein said first circuit obtains said objective refraction data from an input specification device.

7. The apparatus of claim 1 wherein said second circuit obtains said patient age data from a computer.

8. The apparatus of claim 1 wherein said second circuit is constructed to receive said patient age data from an input specification device.

9. The apparatus of claim 3 wherein said third circuit is constructed to receive said eyeglass lens prescription data from an input specification device.

10. The apparatus of claim 3 wherein said third circuit is constructed to receive said eyeglass lens prescription data from an auto lens meter.

11. The apparatus of claim 3 wherein said third circuit is constructed to receive said eyeglass lens prescription data from a computer.

12. The apparatus of claim 1 wherein said autorefractor output adjustment device is implemented with a processor and an associated executable program.

13. The apparatus of claim 1 wherein said autorefractor output adjustment device is implemented as a hardwired circuit.

14. The apparatus of claim 3 wherein said autorefractor output adjustment device selectively identifies myopia data information and hyperopia data information from said objective refraction data and said eyeglass lens prescription data.

15. The apparatus of claim 14 wherein said autorefractor output adjustment device calculates a spherical spectacle value by selectively deriving an increased myopia term and a decreased myopia term from said myopia data information.

16. The apparatus of claim 15 wherein said autorefractor output adjustment device calculates said spherical spectacle value by assigning a full weight factor to said increased myopia term in a young patient as characterized by said patient age data, a substantial weight factor to said increased myopia term in an old patient as characterized by said patient age data, and a sliding scale weight factor for patients therebetween.

17. The apparatus of claim 15 wherein said autorefractor output adjustment device calculates said spherical spectacle value by assigning a full weight factor to said decreased myopia term in an old patient as characterized by said patient age data. a very small weight factor to said decreased myopia term in a young patient as characterized by said patient age data, and a sliding scale weight factor for patients therebetween.

18. The apparatus of claim 14 wherein said autorefractor output adjustment device calculates a spherical spectacle value by selectively deriving an increased hyperopia term and a decreased hyperopia term from said hyperopia data information.

19. The apparatus of claim 18 wherein said autorefractor output adjustment device calculates said spherical spectacle value by assigning a substantially full weight factor to a decreased hyperopia term in a young patient as characterized by said patient age data. a small weight factor to a decreased hyperopia term in an old patient as characterized by said patient age data, and a sliding scale weight factor for patients therebetween.

20. The apparatus of claim 18 wherein said autorefractor output adjustment device calculates said spherical spectacle value by assigning a full weight factor to an increased hyperopia term in an old patient as characterized by said patient age data. a small weight factor to an increased hyperopia term in a young patient as characterized by said patient age data, and a sliding scale weight factor for patients therebetween.

21. The apparatus of claim 15 wherein said autorefractor output adjustment device derives a cyclindrical spectacle value by assigning a second weight factor, which is assigned as a function of said patient age data and optometric clinical judgment. to said objective refraction data and said eyeglass lens prescription data.

22. The apparatus of claim 21 wherein said spherical spectacle value and said cylindrical spectacle value are combined to obtain said eyeglass lens specification.

23. The apparatus of claim 1 wherein said patient age data is characterized by assigning an age factor of zero to a patient older than 45 years. an age factor of 25 to a patient younger than 20 years. and an age factor of between 0 and 25 for patients therebetween.

24. A method of generating an eyeglass lens specification. said method comprising the steps of:

obtaining objective refraction data;

receiving patient age data; and combining said objective refraction data with a weight factor. which is assigned as a function of said patient age data and optometric clinical judgment. to obtain an eyeglass lens specification.

25. The method of claim 24 wherein said combining step includes the step of combining said objective refraction data with eyeglass lens prescription data.

26. The method of claim 25 wherein said combining step includes the step of selectively identifying myopia data information and hyperopia data information from said objective refraction data and said eyeglass lens prescription data.

* * * * *